(12) United States Patent
Sgarzani et al.

(10) Patent No.: US 9,364,237 B2
(45) Date of Patent: Jun. 14, 2016

(54) MEDICAL DEVICE

(75) Inventors: Rossella Sgarzani, Bologna (IT); Rolf Spingler, Jestetten (DE)

(73) Assignee: METESO AG, Schaffhausen (CH)

( * ) Notice: Subject to any disclaimer, the term of this patent is extended or adjusted under 35 U.S.C. 154(b) by 138 days.

(21) Appl. No.: 13/994,500

(22) PCT Filed: Dec. 15, 2011

(86) PCT No.: PCT/EP2011/072886
§ 371 (c)(1),
(2), (4) Date: Jul. 17, 2013

(87) PCT Pub. No.: WO2012/080390
PCT Pub. Date: Jun. 21, 2012

(65) Prior Publication Data
US 2013/0296890 A1    Nov. 7, 2013

(30) Foreign Application Priority Data
Dec. 15, 2010    (EP) .................................... 10195212

(51) Int. Cl.
*A61B 17/08* (2006.01)
*A61B 17/11* (2006.01)
*A61B 17/10* (2006.01)

(52) U.S. Cl.
CPC .............. *A61B 17/11* (2013.01); *A61B 17/08* (2013.01); *A61B 17/10* (2013.01); *A61B 2017/1121* (2013.01); *A61B 2017/1132* (2013.01)

(58) Field of Classification Search
CPC ........ A61B 17/08; A61B 17/10; A61B 17/11; A61B 2017/1121; A61B 2017/1132

USPC .................................................. 606/142, 153
See application file for complete search history.

(56) References Cited

U.S. PATENT DOCUMENTS

| 2,127,903 | A |   | 8/1938  | Bowen |
|-----------|---|---|---------|-------|
| 3,783,873 | A |   | 1/1974  | Jacobs |
| 4,498,476 | A | * | 2/1985  | Cerwin et al. ............... 606/158 |
| 4,593,693 | A |   | 6/1986  | Schenck |
| 4,657,019 | A | * | 4/1987  | Walsh et al. ................. 606/153 |
| 4,728,328 | A |   | 3/1988  | Hughes |
| 5,172,845 | A |   | 12/1992 | Tejeiro |
| 6,843,795 | B1 |  | 1/2005  | Houser |

(Continued)

FOREIGN PATENT DOCUMENTS

EP   1 842495        10/2007
WO   WO 2007/131189  11/2007

OTHER PUBLICATIONS

International Search Report for International Application No. PCT/EP2011/072886 mailed Apr. 4, 2012.

*Primary Examiner* — Katherine M Shi
(74) *Attorney, Agent, or Firm* — Pearl Cohen Zedek Latzer Baratz LLP

(57) ABSTRACT

A medical device is disclosed for joining a first tubular organ (1), such as a blood vessel, to a second tubular organ (2), such as a blood vessel. The kit includes an external tubular scaffold (4) with a removable scaffold handle (7, 18, 19) and a clip (3). In use, the clip (3) and the external tubular scaffold (4) remain outside of the tubular organs (1, 2) being joined. The clip (3) embraces a first longitudinal tubular section (6) of the external tubular scaffold (4) thereby holding together a longitudinal segment of an intima of the first tubular organ (1) and a longitudinal segment of an intima of the second tubular organ (2).

17 Claims, 11 Drawing Sheets

(56) References Cited

U.S. PATENT DOCUMENTS

| | | |
|---|---|---|
| 2002/0058955 A1* | 5/2002 | Blatter et al. ............... 606/153 |
| 2004/0054405 A1 | 3/2004 | Richard |
| 2004/0172043 A1* | 9/2004 | Watson et al. ............... 606/120 |
| 2004/0176783 A1* | 9/2004 | Edoga et al. ............... 606/139 |
| 2004/0230209 A1 | 11/2004 | Masroor |
| 2005/0182430 A1 | 8/2005 | Schenck |
| 2008/0319461 A1 | 12/2008 | Blondeel |

* cited by examiner

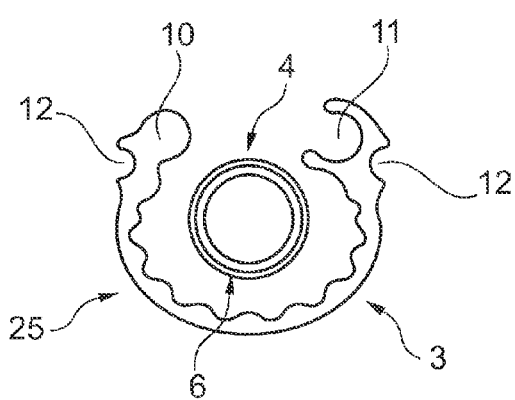
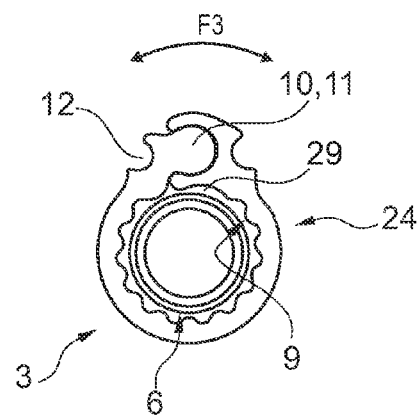
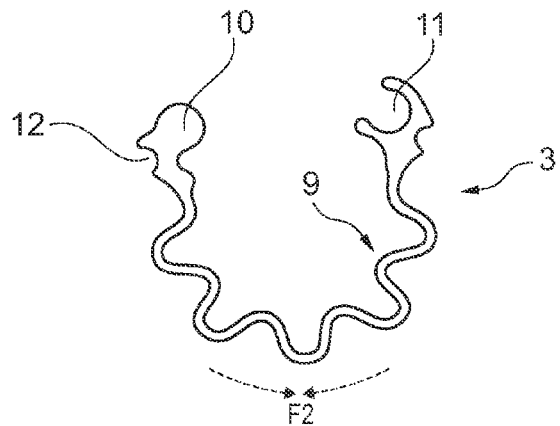
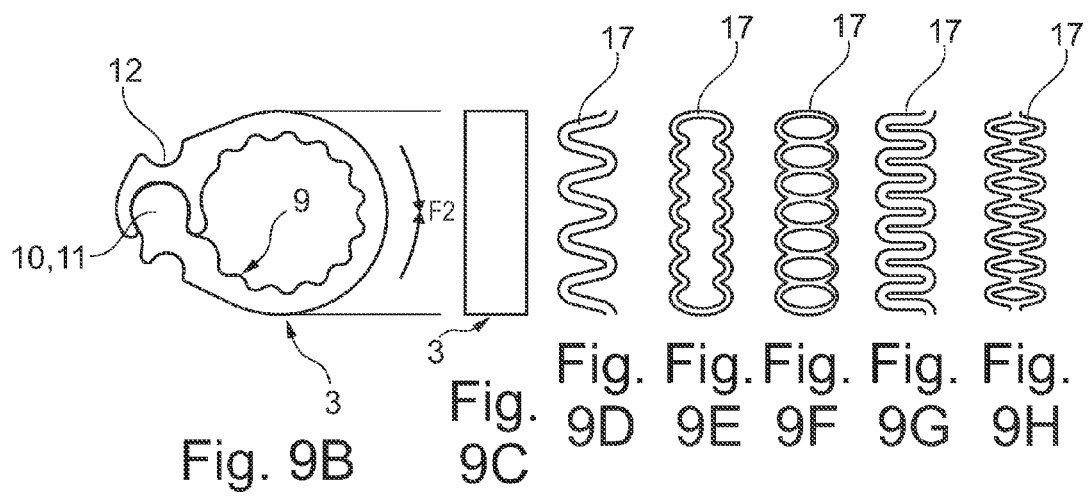

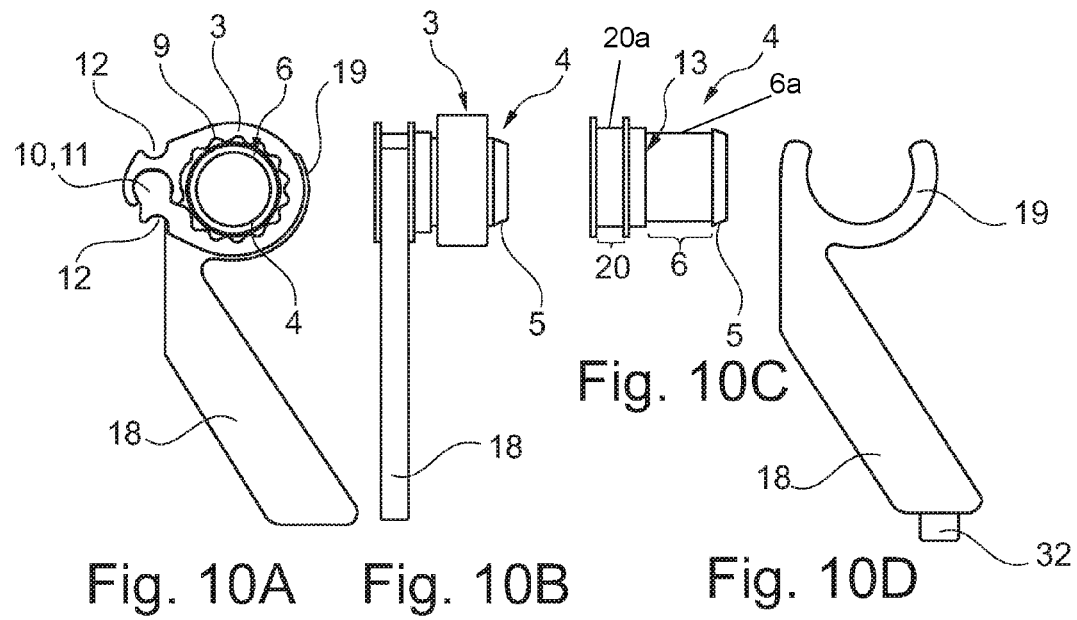
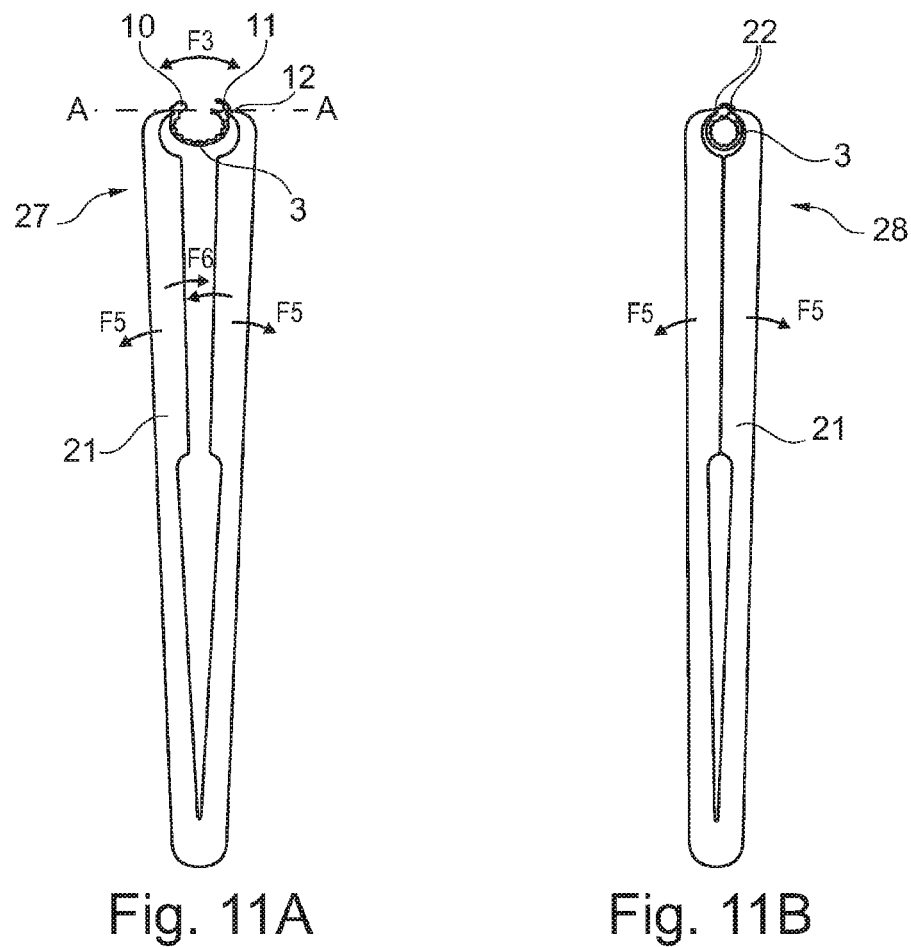

MEDICAL DEVICE

CROSS-REFERENCE TO RELATED APPLICATIONS

This application is a National Phase Application of PCT International Application No. PCT/EP2011/072886, International Filing Date Dec. 15, 2011, claiming priority of European Patent Application No. 10195212.5, filed Dec. 15, 2010, which is hereby incorporated by reference.

DESCRIPTION

The present invention relates generally to the area of sutureless anastomosis of tubular organs, such as blood vessels or intestines or tubular structures of the urogenital tract.

More particularly, the present invention relates to intima-to-intima anastomosis kits for effecting intima-to-intima anastomosis as set out in the pre-characterising portion of claim 1.

BACKGROUND ART

Anastomosis is the connection of two tubular structures or organs. It refers to connections between blood vessels or between other tubular organs such as loops of intestine. Circulatory anastomosis is further divided into arterial and venous anastomosis. An example of surgical anastomosis occurs when a segment of intestine is resected and the two remaining ends are sewn or stapled together (anastomosed), for example Roux-en-Y anastomosis is an intestinal anastomosis procedure. Connecting blood vessels in humans and mammals is a frequently performed procedure. This includes the treatment of peripheral vessel diseases, congenital or developmental deformities and trauma.

Anastomosis is most commonly carried out by a skilled surgeon using sutures to hold the two tubular organs together. Thus, for vascular anastomosis, the surgeons perform each anastomosis by hand suturing with a tiny, curved needle and very fine suture filament. Such a suturing method, however, is very time consuming, even for an experienced surgeon. In some cases the blood flow in the newly joined vessels may be poor, and the surgeon must remove the stitches and repeat the suturing procedure. In some surgical procedures, the total time required for suturing is very substantial, increasing ischemia time and/or resulting in prolonged anaesthesia time and increasing the cost of the surgical procedure.

For end-to-side type grafting procedures the surgeon attaches the open end of a graft vessel to the side of a target vessel. In a preferred type of suturing method for end-to-side anastomosis of blood vessels, the surgeon passes a needle through the wall of the first vessel (such as the coronary artery) from the inside to the outside, and then passes it from the outside to the inside of the second vessel (such as the graft vessel), so that when the suture is drawn tight, the inside walls of the vessels come together, intima-to-intima. This ensures that the vessels heal together properly with a smooth layer of endothelial cells formed on the inside of the anastomosis. The surgeon typically places a single stitch in this manner at each of the heel and toe locations of the anastomosis, and then makes a running stitch on each half of the anastomosis between the heel and toe.

Surgeons commonly use an end-to-end type of anastomosis for joining together larger hollow organs such as bowel, and for some heart bypass procedures where the arterial flow is completely occluded by stenosis in a diseased artery. End-to-end type anastomosis is also used in microsurgical procedures (microvessel (<3 mm) anastomosis)—such as when replacing severed limbs or fingers or in autologous free tissue transplantation or composite tissue allografting etc.

In recent years, surgeons have been using alternative, minimally-invasive means of access to reduce the size of the surgical wound created. In such procedures, the surgical opening and visibility are significantly reduced, and hand suturing is more difficult. Other new developments in surgical procedures have made conventional suturing even more difficult. For example, some surgeons now perform bypass surgery on beating hearts to avoid the complications associated with using a heart lung bypass machine.

The literature contains disclosures of a number of devices for augmentation of suturing techniques. These devices attempt with varying degrees of success to reduce the difficulty in repeatedly passing a needle and thread through organ walls. However, the main disadvantage of using sutures remains that the success and thus patency rate of the procedure is directly related to the skills and dexterity of the surgeon. Also, the smaller the vessels are that need to be connected the more time consuming the procedure is. As long as microsurgery and free flap surgery in reconstructive procedures are time-consuming and dependent on technical skills, they will never be very popular.

For many years, many different attempts have been made to provide an apparatus that would allow end-to-end (and/or end-to-side) anastomosis of tubular organs without the use of sutures (i.e. suturelessly).

Some success has been achieved in this area with relatively large tubular organs such as the intestines, for which bowel staplers have been developed (see, for instance, U.S. Pat. No. 5,172,845). However such stapling devices are not generally suitable for use with much smaller and/or much more sensitive vessels such as blood vessels.

Another approach to end-to-end anastomosis has been to provide a tubular prosthesis to which each end of the two tubular organs are joined (see, for example, U.S. Pat. No. 4,728,328).

Also, in some prior art systems, a tubular element may be inserted into each end of the two tubular organs to be joined and the tubular organs may be fastened onto the tubular element (see, for example, U.S. Pat. No. 2,127,903, WO 2007/131189 and US 2004/0230209). If used in such a way that the ends of the vessel heal to one another (e.g. when joining using sutures around such a tubular element), it has been suggested that such a tubular element might be made from a bioresorbable material (e.g. U.S. Pat. No. 2,127,903). Disadvantages of such systems include the fact that the interior diameter available for flow of body fluids (e.g. blood) is reduced by the tubular element. Such a diameter-reduction can be material when anastomosing relatively small vessels. Also, in such prior art systems, the tubular element is within the flow-path of the vessel and must therefore have suitable, very-hard-to-achieve biocompatibility material properties to prevent its causing further medical problems for the patient (e.g. for blood vessels, such effects might include creating emboli that could migrate into the systemic circulation.

U.S. Pat. No. 4,593,693 and US 2005/0182430 disclose a different approach in which a ring element is provided that, in use, remains at all times outside of the flow-path of the tubular organs. In this approach, an end of a first tubular organ to be joined is threaded through the ring element, folded back on itself and hooked onto radially-outwardly projecting spikes on the ring element, which are provided for this purpose. An end of a second tubular organ to be joined is then pulled over the ring element and hooked over the same spikes. This methodology thus creates desirable intima-to-intima contact of the organs being joined and keeps the ring element itself out of the flow-path of the vessels. The ring element also acts as an external tubular scaffold—holding the vessels open at the joint, though remaining outside of the vessels at all times. However, this system has a number of disadvantages including that, over time, the spikes may cause undesirable internal damage to other organs of the patient near to the anastomosis joint—particularly in bodily locations where many small delicate organs are very close to each other and often in motion (e.g. blood vessels in a finger). Also, for vessels that may be in motion when in use, there is a risk that a vessel may become unhooked and, at best, cause a need to repeat the surgical procedure. Another disadvantage of the 'hooked on' system is that unintended leakage may occur at the joint prior to full healing and, depending on the particular type and location of the particular vessels, this may cause considerable undesirable patient complications.

Still another approach is disclosed in EP 1 842 495, which, to the best knowledge of the inventors of the present application, represents the only sutureless anastomosis system that has ever become available on the open market. In this system, two rings with axially directed metal spikes are connected, each to the end of one of the two tubular organs to be anastomosed. A rather complex applicator device is then used to mechanically force the two rings together such that the spikes of each ring engage and lock into place the other ring. Although this system has enjoyed a certain amount of clinical success, it has several disadvantages including the continued use of spikes as outlined above and the fact that the form and size of the applicator device can make it difficult to make the joint in applications providing tight environments. Also, the relatively large dimensions of the rings makes it prone to tip over and thereby constrict or compress the vessel.

It is an objective of the present invention to provide an anastomosis kit and method that allows sutureless anastomosis and overcomes some of the disadvantages of prior art systems.

SUMMARY OF THE INVENTION

These objectives are met by an intima-to-intima anastomosis kit comprising the features of claim 1 of the present application and by an intima-to-intima anastomosis method comprising the features of claim 22 of the present application.

The intima-to-intima anastomosis kit according to the present invention comprises an external tubular scaffold, a removable scaffold handle and a clip. The external tubular scaffold comprises a first longitudinal tubular section which the clip embraces when the clip is in a closed state. Before removal, the removable scaffold handle is displaced longitudinally from the first longitudinal tubular section.

In use, a segment of a first tubular organ is threaded through an interior passage of the external tubular scaffold—using the removable scaffold handle to hold the external tubular scaffold while doing so. This tubular organ is then folded back over itself to form a cuff portion, which is placed around the outside of the first longitudinal tubular section of the external tubular scaffold. A segment of a second tubular organ is then placed around the cuff portion. Finally, a clip is placed around the second tubular organ, the cuff portion and the first longitudinal tubular section of the external tubular scaffold, and closed such that the clip embraces these and forms a good intima-to-intima anastomosis joint between the first tubular organ and the second tubular organ.

The intima-to-intima anastomosis kit of the present invention has the advantage that it provides a system that is simple and relatively fast to apply and a substantially fluid-tight, secure joint may be formed without using spikes that might damage neighbouring organs. Thus, the main advantages of the intima-to-intima anastomosis kit of the present invention are providing better, substantially leak-free anastomosis; saving time during surgery; and making the task of anastomosis more reliably and safely reproducible even at levels of operator dexterity which are less than the highest achievable level.

The intima-to-intima anastomosis kit of the present invention also has the advantage that all elements of the kit remain, at all times, outside of the flow-path of the tubular organs being anastomosed. This both reduces danger to a patient (in particular reducing blood-clotting risks) and lowers biocompatibility requirements of the material used for the parts of the anastomosis kit which are to remain in a patient's body.

The intima-to-intima anastomosis kit of the present invention also has the advantage that it brings the interior surfaces (i.e. 'intima') of the tubular organs which are to be joined into close contact to maximise the chances of effective and rapid healing and patient recovery.

The intima-to-intima anastomosis kit of the present invention also has the advantage that the parts of the kit which are to remain in a patient's body may preferably be made as longitudinally short as possible to allow for use in as many different procedures as possible and to minimise the amount of foreign material placed inside a patient.

Further desirable and preferred embodiments of the present invention are set out in claims 2 to 21. These and other preferred embodiments are also described in the following detailed description, in which some examples of embodiments of the invention are given with respect to one possible application of the present invention which, by way of example, involves the microsurgical anastomosis of blood vessels.

An understanding of the further objectives and advantages of these and other embodiments of the invention may be gained from the following drawings and detailed description.

BRIEF DESCRIPTION OF THE DRAWINGS

The drawings used in elucidating the example embodiments of the invention show:

FIGS. 8A, 8B Schematic representations of a further embodiment of a clip with a locking device according to the invention (8A: open and 8B: shut);

FIGS. 9A, 9B, 9C, 9D, 9E, 9F, 9G, 9H Schematic representations of further embodiments of clips with circumferential clip-constrictive returning force generation according to the invention;

FIGS. 10A, 10B, 10C, 10D Schematic representations of further embodiments of the invention with a snap-on/snap-off removable scaffold handle according to the invention;

FIGS. 11A, 11B Schematic representations of an embodiment of a clip applicator according to the invention (11A: open and 11B: shut);

In the drawings, analogous parts have, in general, been labelled with the same reference numbers.

DETAILED DESCRIPTION

Figure 1:
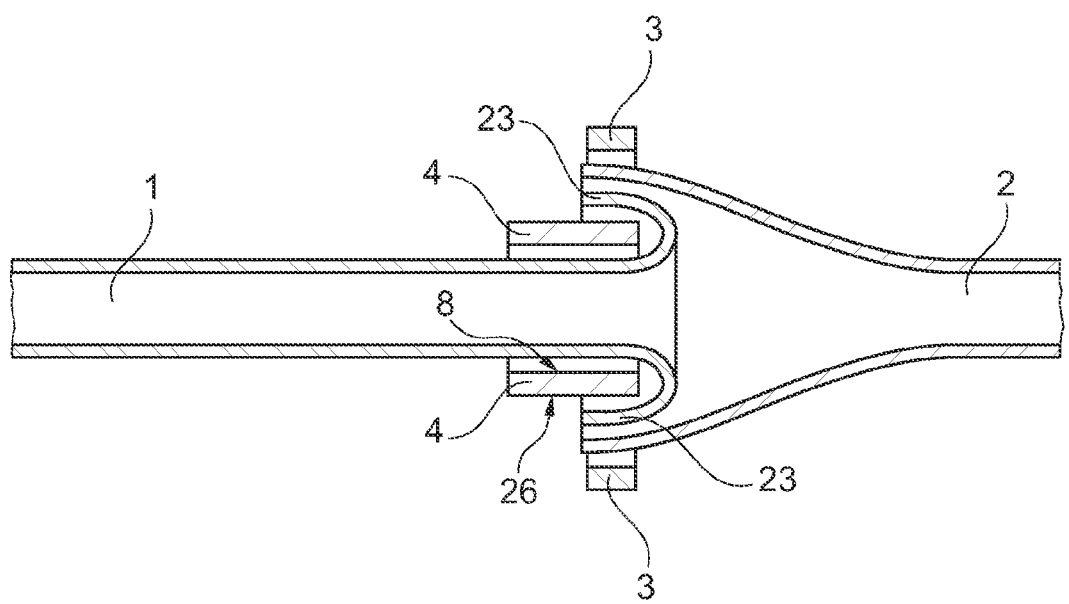
FIG. 1 Schematic cross-sectional representation of some of the parts of an intima-to-intima anastomosis kit according to an embodiment of the invention being put in place on two blood vessels (clip open)
Figure 2:
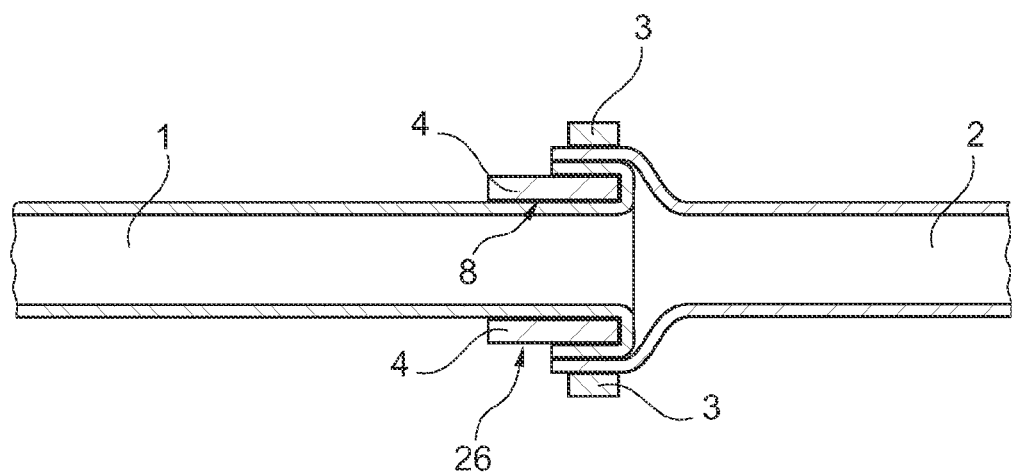
FIG. 2 Schematic cross-sectional representation of some of the parts of an intima-to-intima anastomosis kit according to an embodiment of the invention being put in place on two blood vessels (clip closed)

FIGS. 1 and 2 show in schematic form, the interoperational functionality of an external tubular scaffold 4 and a clip 3 when used to anastomose a first tubular organ 1, such as a blood vessel, in end-to-end fashion with a second tubular organ 2, such as another blood vessel.

In FIG. 1, the first tubular organ 1 has been threaded through the external tubular scaffold 4, such that an inner tubular surface 8 of the external tubular scaffold 4 is adjacent to the exterior surface of the wall of the first tubular organ 1. A cuff portion 23 of the first tubular organ 1, formed by folding the first tubular organ 1 back over itself, has been placed concentrically around an exterior surface 26 of the external scaffold structure 4 and a second tubular organ 2 has been placed concentrically around the cuff portion 23. An open clip 3 has been placed concentrically around the second tubular organ 2 and the cuff portion 23 and the exterior surface 26 of the external tubular scaffold 4.

FIG. 2 depicts the same items as in FIG. 1, except that in FIG. 2, the clip 3 has been closed such that it is in a closed state and now embraces the second tubular organ 2, the cuff portion 23 of the first tubular organ 1 and the exterior surface 26 of the external tubular scaffold 4.

It is to be noted that both the external tubular scaffold 4 and the clip 3 are exterior to the two tubular organs 1, 2. Thus, as long as the joint holds, anything that flows through or is contained in the two tubular organs 1, 2 would never be able to contact either the external tubular scaffold 4 or the clip 3. Also, if the external tubular scaffold 4 and/or the clip 3 were made from bioresorbable or biodegradable material, all bioresorption would occur outside of the tubular organs 1, 2. Following such bioresorption, all that would be left in a patient's body is a strong intima-to-intima joint of two tubular organs.

Also to be noted is that it is the internal surfaces (i.e. the 'intima'—in this specification, the term 'intima' is to be interpreted as referring to the innermost coat of any tubular organ which is to be anastomosed) of each of tubular organs 1, 2 which are held together by the external tubular scaffold 4 and the clip 3. Such intima-to-intima anastomosis gives the highest possible chance of ensuring that the tubular organs 1, 2 will heal together properly with a smooth layer of endothelial cells formed on the inside of the anastomosis.

Figure 3:
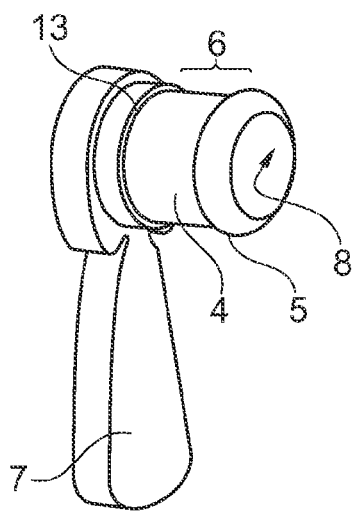
FIG. 3 Schematic representation of an embodiment of an external tubular scaffold with frangibly removable scaffold handle according to the invention.

FIG. 3 shows an embodiment of an external tubular scaffold 4 with a removable scaffold handle 7. The removable scaffold handle 7 is frangibly attached such that it may be broken off or cut when no longer required.

To further facilitate breaking of the removable scaffold handle 7, the handle 7 might be notched or scored along a line 7a. A first longitudinal section 6 of the external tubular scaffold 4 is provided for receiving the clip 3.

As used in this specification, the terms 'longitudinal' and 'axial' are used to refer to lines of direction substantially along the length of the first tubular organ 1, the second tubular organ 2 and the external tubular scaffold 4 (and the clip 3, when it is in position concentric to the external tubular scaffold 4). That is to say, longitudinal/axial refer to lines of direction substantially parallel to the lines of direction B and C in FIG. 12 and FIG. 14A respectively. The terms 'radial' and 'perpendicular' are used to refer to lines of direction at substantially 90° to the longitudinal/axial direction. The term 'circumferential' relates, in general, to lines of direction which are circumferential with respect to a generally longitudinal/axial line of direction.

In the embodiment of FIG. 3, the first longitudinal section 6 is in the form of a relatively wide groove with, on one side a side wall 13 and on the other side a nose 5 which is shaped to make both a folding back (or flipping over) of an internal organ to form a cuff portion and an insertion into another internal organ easier. Such a relatively wide groove provides a longitudinally extended area over which tubular organs may be gripped, allowing a spreading of the mechanical load on organ walls when in use. The internal surface 8 of the external tubular scaffold 4 is smooth and has a diameter wide enough to allow a first tubular organ to pass easily through it without any need for compressing the organ.

Figure 4:
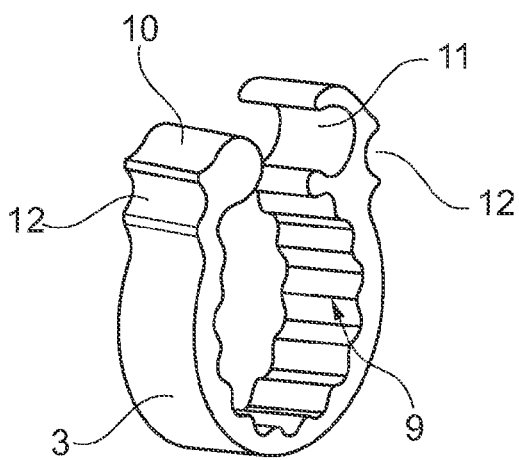
FIG. 4 Schematic representation of an embodiment of a clip according to the invention.

In FIG. 4, a clip 3 for use with the external tubular scaffold 4 of FIG. 3 is shown. This clip 3 has an interior clamping-surface 9 which is ribbed or fluted in a longitudinal direction. The clip 3 of FIG. 3 also has a locking device 10, 11 which consists of a male interlocking feature 10 and a female interlocking feature 11. In the embodiment of FIG. 4, the interlocking features 10, 11 may be snapped together to interlock with each other and thus lock the clip 3 into a closed state. The locking device 10, 11 may be reopened after closing by applying a certain force to pry the locking device 10, 11 apart or by pushing the interlocking features 10, 11 longitudinally in opposite directions. Two specially formed indentations 12 are formed in the clip 3 which are for use in holding the clip 3 in a clip applicator such as a pair of specially-designed forceps.

Figure 5:
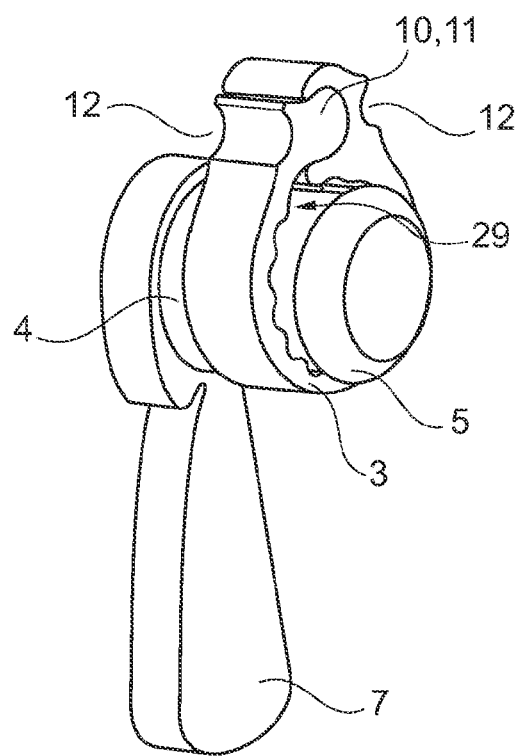
FIG. 5 Schematic representation of the clip, external tubular scaffold & frangibly removable scaffold handle of FIGS. 3 & 4 together.

In FIG. 5, the clip 3 of FIG. 4 is shown in position around the external tubular scaffold of FIG. 3. The same elements are present as in FIGS. 3 & 4 and will not be redescribed here.

It is to be noted that in FIG. 5, a circumferential clamping-gap 29 is defined between a part of the first longitudinal section 6 of the external tubular scaffold 4 and the interior clamping-surface 9 of the clip 3. In use, this gap is filled by a cuff portion of a first tubular organ and a segment of a second tubular organ. The walls of such tubular organs have thicknesses that may vary—both longitudinally and circumferentially. For this reason, it is desirable to have a clamping gap 29 which is not uniform in its radial dimension. Thus, as seen in FIG. 4, in this embodiment, the interior-clamping surface 9 of the clip 3 is ribbed or fluted in the longitudinal direction. Other surface patterns which create uneven textures (not shown) would also have the desired effect of creating a clamping-gap 29 with a varying radial dimension. Thus, circumferential ribs might be used or some other textured pattern. Also, the patterning, ribbing, fluting or texturing might also be executed on an exterior clamping-surface of the first longitudinal section 6 of the external tubular scaffold 4 either instead of or in addition to that on the interior clamping-surface 9 of the clip 3 and the same desired effect would be achieved. Since such a varying clamping-gap 29 can be used over a range of organ wall thicknesses, the provision for such a clamping-gap 29 can also enable a reduction in need for providing such a large variety of sizes of clips 3 to cope with different organ wall thicknesses. This has benefits both for the surgeon and for the kit supplier in terms of cost and of improved ease of use in an operating theatre environment.

FIG. 6A to 6D show a number of embodiments of clips 3. These clips 3 have spring-force-generating elements 15 which act to generate an opposing clip-closing returning force F1 if the clip 3 is displaced from a closed state 24 towards an open state 25. Thus, the clips 3 shown in FIG. 6A to 6D have a clip rest state in the closed state 24 and any attempt to displace any of these clips 3 from the closed state 24 [i.e. the clip rest state for these clips] will cause an opposing clip-closing returning force F1 to be generated by the clip 3.

Figure 6A:
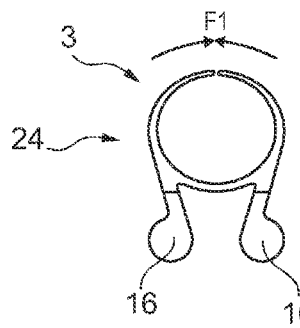
FIGS. 6A, 6B, 6C, 6D Schematic representations of further embodiments of clips according to the invention.
Figure 6B:
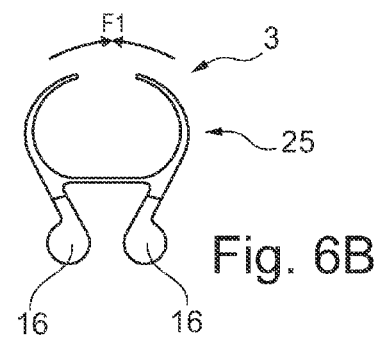
Figure 6C:
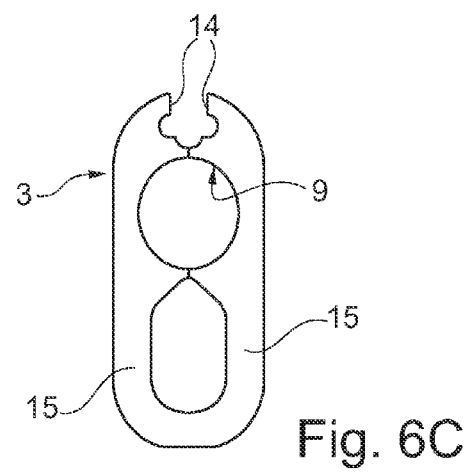
Figure 6D:
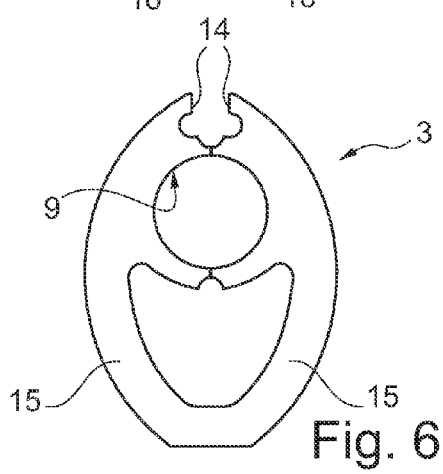

On the embodiments of FIG. 6C and FIG. 6D, internal facing opening surfaces 14 are provided which allow a kit user to use a tool (or their fingers) to pry the clip 3 open in order to be able to place it in a position where is may embrace a first longitudinal section 6 of an external tubular scaffold 4.

Figure 18A:
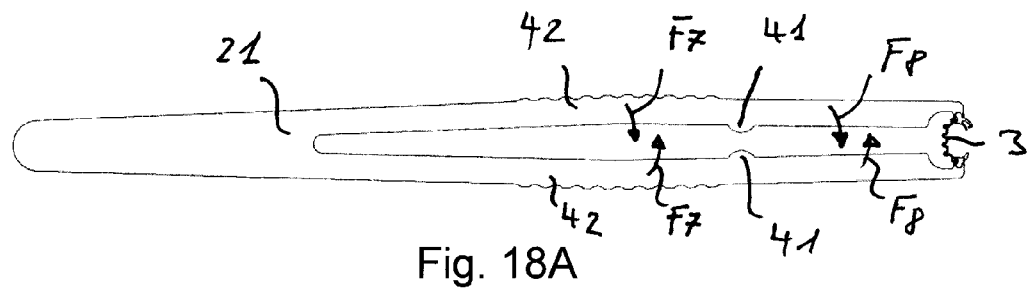
FIGS. 18A, 18B, 18C Schematic representations of an embodiment of a further clip applicator according to the invention (18A: open, 18B: shut and 18C: remove)
Figure 18B:
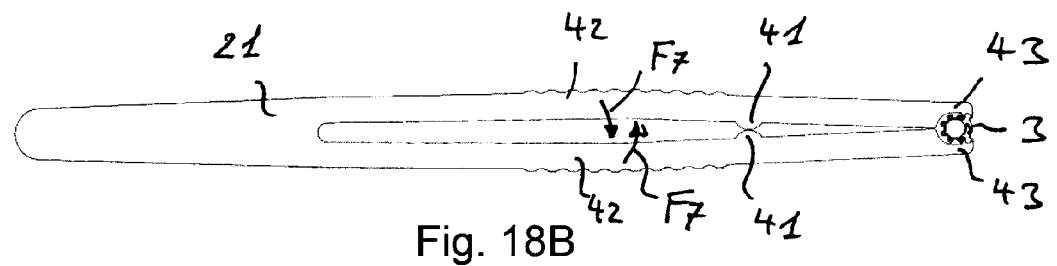
Figure 18C:
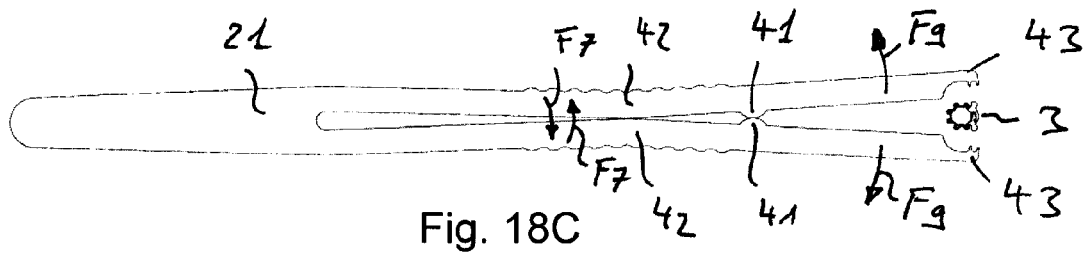

On the embodiments shown in FIG. 6A and FIG. 6B, two opening lobes 16 are provided which allow a kit user to squeeze these opening lobes 16 together in order to move the clip 3 from a closed state 24 to an open state 25. The clip applicator 21 disclosed in FIGS. 18A, 18B, 18C is for example suitable to place the clip disclosed in FIG. 6A and FIG. 6B on the tubular scaffold 4. The clip locator recesses 45 of the clip applicator 21 would be acting onto the lobes 16 to manipulate the clip 3.

It is worth noting that in the closed state 24 each of the embodiments of the clip 3 is generally 'O'-shaped. It is to be understood of course that, in this context, 'O'-shaped is a term which is intended to be interpreted broadly, in the sense that the interior clamping-surface of a clip 3 may be effectively circular in form, as shown, though it may also adopt an infinite variety of other closed shapes (e.g. square, with rounded corners etc.) and also the form of the clamping-surface 9 in its closed state may be fully-closed in an 'O'-shape or it may be close to being closed. For instance, in the embodiment shown in FIGS. 6A and 6B with the two opening lobes 16, the closed state 24 of the clip is generally 'O'-shaped even though the clip is not fully forming an 'O'—due to a small gap at the side of the clip opposite to the opening lobes 16. Also, when the clips 3 of FIG. 6A to 6D which generate an opposing clip-closing returning force F1 are positioned around the first longitudinal tubular section 6 of an external tubular scaffold 4, with organ walls there between, the closed state 24 of such a clip 3 may or may not fully join together, but nonetheless, the closed state of such a clip is intended to be considered as 'O'-shaped. It is preferable, though not absolutely necessary, that clips 3 such as those shown in FIG. 6A to 6D should, as far as possible, be of an appropriate size that they fully or nearly-fully join together when positioned in a closed state 24 around the first longitudinal tubular section 6 of an external tubular scaffold 4, with organ walls there between.

It is also worth noting that in the open state 25 the clips 3 are generally 'C'-shaped. The mouth-opening of the generally 'C'-shaped clip 3 in its open state 25 is sufficiently wide to enable a relevant part (e.g. the first longitudinal tubular section 6) of an external tubular scaffold 4 and/or a first tubular organ 1 and/or a second tubular organ 2 to be passed through the mouth-opening in a generally radial direction. The mouth opening of the clip 3 in its open state 25 may be as wide as the maximum diametrical dimension of the first longitudinal section 6 to allow for direct perpendicular clip application. However, smaller mouth openings may also be used or even preferred. In use, the second tubular organ 2 may be flattened somewhat to allow such a clip 3 with a smaller mouth opening to be brought concentrically around the second tubular organ 2 and the clip 3 may then be moved longitudinally into place to embrace the first longitudinal tubular section 6 of the external tubular scaffold 4.

Figure 7A:
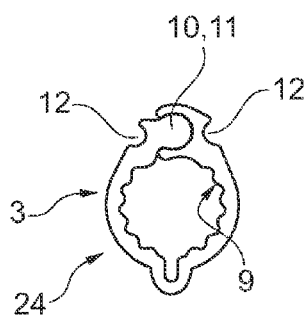
FIGS. 7A, 7B, 7C, 7D, 7E Schematic representations of further embodiments of clips with locking devices according to the invention.
Figure 7B:
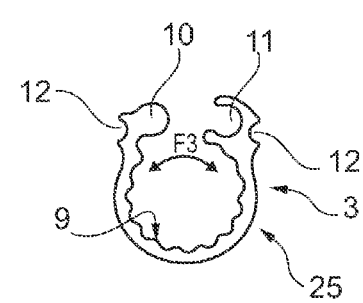
Figure 7C:
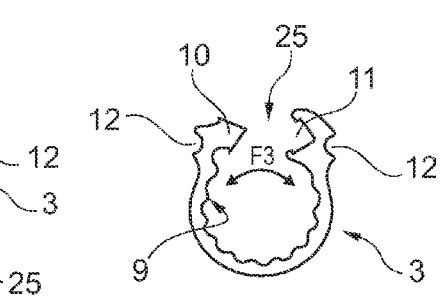
Figure 7D:
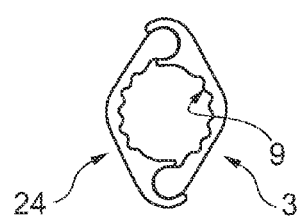
Figure 7E:
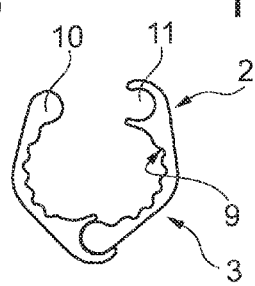

FIG. 7A to 7E show a number of embodiments of clips 3 with locking devices 10,11 for holding such clips in a closed state—generally similar to those shown in FIG. 4 and described more above. In FIG. 7A to 7E, it may be seen that various designs of male interlocking features 10 and female interlocking features 11 may be used. In general, a locking device which holds securely shut, but is easily releasable is to be preferred. Such locking devices 10,11 may be implemented [not shown] on clips 3 which generate an opposing clip-closing returning force F1, such as those of FIG. 6A to 6D. The clips 3 shown in FIG. 7A to 7C have a clip rest state in an open state 25. Such clips may have a clip rest state in which the mouth-opening of the 'C'-shaped open clip is larger than the maximum diametrical dimension of the first longitudinal section 6 of an external tubular scaffold 4—such that such a clip 3 may be placed directly in position in its open state 25 in a radial direction with respect to the external tubular scaffold 4. In some applications, a clip 3 with a smaller mouth opening may be used or even preferred, which may then be partially opened over a flattened vessel/tubular organ 2 and moved longitudinally into position. When clips 3 such as those shown in FIG. 7A to 7C are displaced from their open state 25 clip rest state towards the closed state 24, an opposing clip-opening returning force F3 is generated by the clip.

In other embodiments (not shown), returning forces such as an opposing clip-closing returning force F1 like that in FIG. 6A to 6D or an opposing clip-opening returning force F1 like that in FIG. 7A to 7C (or an opposing circumferentially-directed clip-constrictive force F2 like that in FIGS. 9A and 9B, as described below) may be generated by additional spring-force generating means suitably arranged and adapted.

FIGS. 8A and 8B show an end view of a clip 3 similar to those shown in FIGS. 4, 5 & 7B in both its open state 25 and its closed state 24 around a first longitudinal section 6 of an external tubular scaffold 4. It is to be noted that the clamping-gap 29 formed is substantially circumferential, in that it goes around as much of the circumference as possible, though may not achieve full coverage of the whole circumference (either as shown in FIG. 8B, where the interior clamping surface 9 does not form a perfect 'O', despite the clip 3 being 'O'-shaped or (not shown) as might be expected if a clip 3 which generates an opposing clip-closing returning force F1 such as the clips shown in FIG. 6A to 6D were to not fully join together in the clip's closed state (despite the clip being generally 'O'-shaped, as explained above). In general terms, the clip embraces the first longitudinal section 6 of the external tubular scaffold 4. Thus, just as with a human embrace, the clip 3 may, as shown in FIGS. 8A and 8B, 'put its arms around' the first longitudinal tubular section 6 and notionally 'join its hands behind the back' of the first longitudinal tubular section 6. However, it is also fully possible that an embrace does not involve 'joining hands behind the back' and clips may be used (not shown) which, for example only partially 'circumferentially cover' the exterior clamping-surface 26. Thus the term 'embrace' is intended to be interpreted broadly in the sense of 'an action similar to a human embrace' in which arms are put around someone to be embraced and on 'closing' of the embrace, a certain squeezing force is exerted on the person being embraced. Instead of the indentations 12, the clip 3 may have applicator locator lobes 44 as disclosed in FIGS. 19A, 19B, 19C to be connected with a clip applicator 21 as disclosed in FIGS. 18A, 18B, 18C.

As mentioned above, the walls of tubular organs have thicknesses that vary—both longitudinally and circumferentially. It is desirable to be able to accommodate this within an intima-to-intima anastomosis device which effectively clamps together such walls. FIGS. 9A and 9B show embodiments of clips 3 according to the present invention which allow for such accommodation by providing clips 3 which have a circumferential clip rest state. Such a circumferential rest state may be instead of or in addition to other clip rest states (e.g. vis-à-vis opening/closing of a clip 3). Thus, the embodiments of clips 3 shown in FIG. 9A to 9H may, when closed, still be expanded along their circumference either through a suitable shaping of a clip 3 in a plane perpendicular to the central axis of rotation of the clip or through a suitable forming of the circumference of the clip. Such a suitable forming of the circumference of the clip is perhaps most easily understood through thinking of the vaguely analogous situation of an elastic stretchable band for example as commonly used on some watchstraps. In FIG. 9C to 9H, some suitable circumferential formings 17 are schematically depicted as projections of a side-view of a clip 3. FIG. 9A shows an embodiment in which a clip 3 is suitably shaped, as a sort of circumferential wavy line, in a plane perpendicular to the central axis of rotation of the clip 3. Thus, while such embodiments can be displaced from their circumferential rest state in a circumferentially expansive direction, when such displacement occurs, in each of the clip embodiments shown in FIG. 9A to 9H, an opposing circumferentially-directed clip-constrictive force F2 is generated. Thus, such a clip 3 will accommodate varying thicknesses of organ walls between them, but will still apply a desirable constrictive clamping force to these organ walls to further increase the security of the intima-to-intima anastomosis.

FIGS. 10A to 10D show schematic representations of embodiments with an external tubular scaffold 4 a clip 3 and a removably attachable removable scaffold handle 18,19. In the embodiments shown in FIG. 10A to 10D, a first longitudinal section 6 of the external tubular scaffold 4 having an outer surface 6a is provided for receiving the clip 3, and a second longitudinal section 20 having an outer surface 20a is provided on the external tubular scaffold 4. Onto the second longitudinal section 20 having the outer surface 20a, a generally 'C'-shaped portion 19 of the removable scaffold handle 18,19 may be snapped onto and snapped off of. The removable scaffold handle 18,19 of FIGS. 10A, 10B and 10D is thus 'snappably removable' on and off of the second longitudinal tubular section 20. Other features referenced in FIG. 10A to 10D have been described with reference to previous figures—other than tab 32 in FIG. 10D, the purpose of which is best understood from the text below describing the steadying plate of FIGS. 15 and 16.

FIGS. 11A and 11B show embodiments in which a clip applicator 21 releasably holds a clip 3. Analogously to some embodiments of clips 3, the clip applicator may be made such that it has a clip applicator rest state and that displacement of the clip applicator away from the clip applicator rest state causes clip applicator returning forces F5, F6 to be generated. It is to be noted (and is equally true for clip embodiments) that such returning forces F5, F6 (or for clip embodiments: F1, F2, F3) may exist for a single embodiment in more than one direction. For the embodiments shown in FIGS. 11A and 11B, the clip applicator 21 has a clip applicator rest state that is slightly further closed than in the depicted clip-applicator-open and clip-applicator-holding state 27 in which the clip 3 is held in the clip applicator 21 in an open state 25 and the clip rest state is slightly further open than in this depiction. Stated otherwise: when the clip 3 is in its rest state, the distance across the mouth-opening of the open clip 3 between the surfaces of the two specially formed indentations 12 is slightly more than the distance between the tips of the clip applicator 21 which are intended to engage with the two specially formed indentations in the embodiment depicted in FIG. 10A. Thus the clip applicator 21 needs to be opened slightly from its clip applicator rest state to accommodate the clip 3 and the clip 3 needs to be closed slightly from its clip rest state to be mounted in the clip applicator 21. The end effect of this is that when such a clip 3 is mounted into such a clip applicator 21, directionally-opposing returning forces are generated F3,F6—namely one opposing clip-opening returning force F3 and one opposing clip-applicator-closing returning force F6. By means of these returning forces, the clip 3 of FIG. 10A is releasably held. It is to be noted, again that on the one hand an opening of the clip applicator beyond its, in this case generally open, clip applicator rest state causes the generation of an opposing clip-applicator-closing returning force F6 which tends to close the clip applicator towards the clip applicator rest state, while, on the other hand a closing of the clip applicator 21 beyond its clip applicator rest state causes the generation of an opposing clip-applicator-opening returning force F5.

Thus, when the clip applicator 21 in FIGS. 11A and 11B is pushed into a closed state 28, there is an opposing clip-applicator-opening returning force F5 which is generated.

Figure 12:
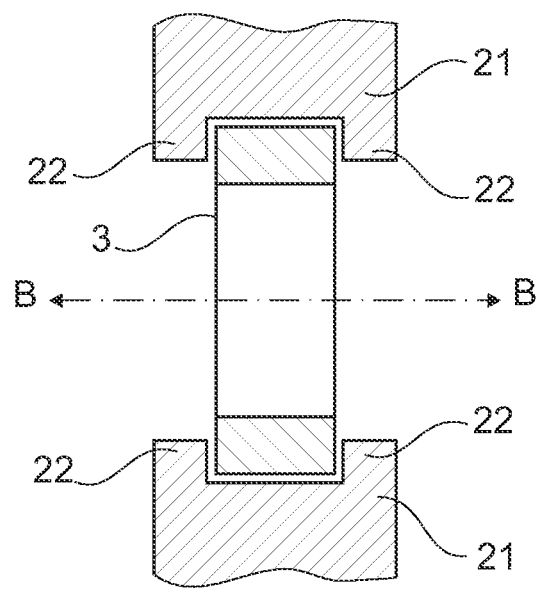
FIG. 12 Schematic sectional representation of an embodiment of a clip applicator according to the invention depicting longitudinal positioning.

Longitudinal location lobes 22 on the clip applicator 21 are shown in FIGS. 11A and 11B and also, in another view in FIG. 12 which is a schematic representation of a cross-sectional view of the embodiment shown in FIG. 11A, along the line A-A.

In FIGS. 11A, 11B and FIG. 12, a clip 3 is held in a clip applicator 21. The clip applicator 21 has longitudinal location lobes 22 which ensure that the clip 3 is held at a predetermined location with respect to the clip applicator 21 along a general longitudinal line of direction of a central axis of rotation B-B of the clip 3.

Figure 13:
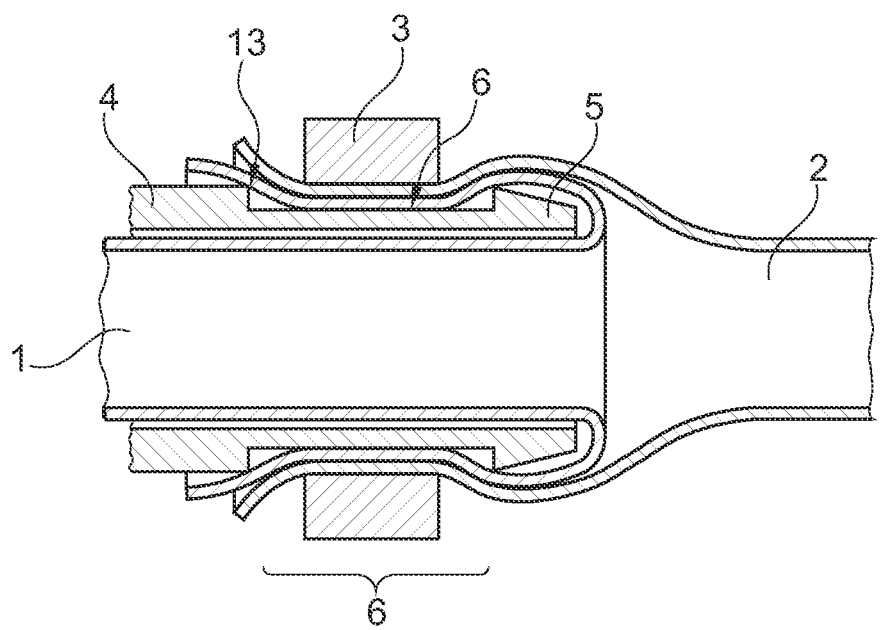
FIG. 13 Schematic sectional representation of an embodiment of the invention depicting example of need for longitudinal positioning.

FIG. 13 shows a schematic cross-sectional representation of a clip 3 in a closed state embracing a first longitudinal tubular section 6 of an external tubular scaffold 4. Between the clip 3 and the external tubular scaffold 4 two longitudinal segments of the walls of a first tubular organ 1 and a second tubular organ 2 are gripped. In the embodiment of FIG. 13, the first longitudinal tubular section 6 is delimited by features (viz. a side wall 13 and a nose 5) which have sharp or relatively sharp features. In such an embodiment, it is highly desirable that the clip 3 should not be 'brought down' on such sharp features as this could cause undesirable damage to the organs—either immediately or over time. Many other embodiments are possible in which, for various reasons, it is desirable to close the clip around a particular longitudinal tubular section of the external tubular scaffold 4 (i.e. centred on the first longitudinal tubular section 6).

Figures 14A, 14B:
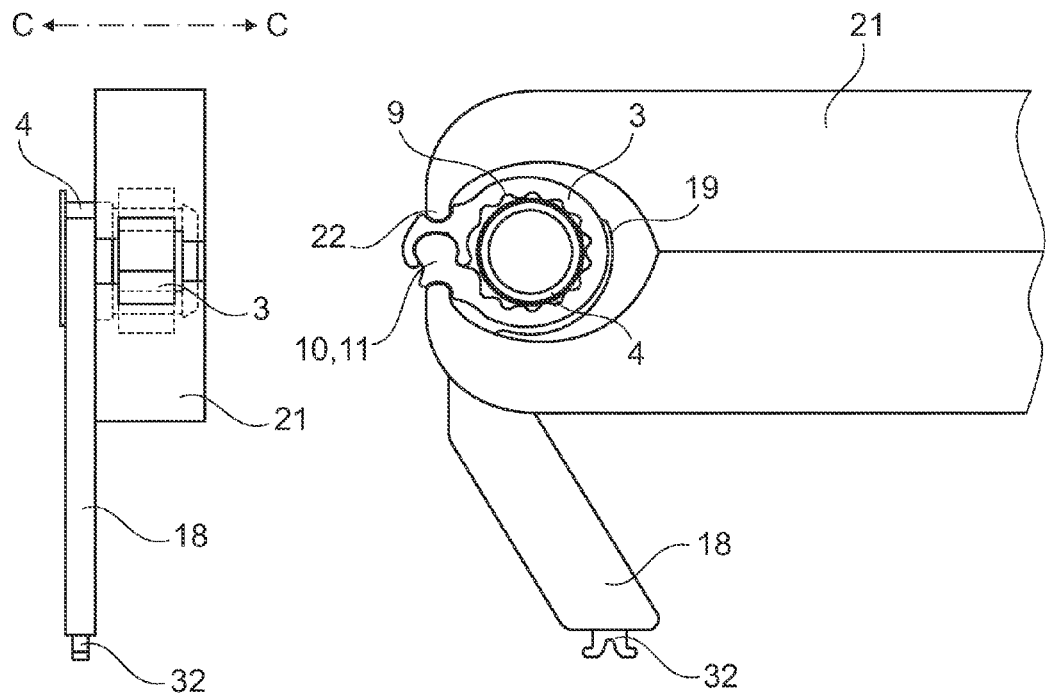
FIGS. 14A, 14B Schematic representations of a clip-guiding embodiment of the invention.

As shown in FIGS. 14A and 14B, in some embodiments of the present invention, various elements of the intima-to-intima anastomosis kit may be used to facilitate a guiding of the clip 3 towards a predetermined longitudinal position with respect to the external tubular scaffold 4. Alternatively (not shown) additional longitudinal guide members may also be provided to achieve the same aim.

In the embodiment shown in FIGS. 14A and 14B, the snap-on/snap-off removable scaffold handle 18,19 acts as a longitudinal guide member, working in conjunction with the clip applicator 21, clip 3 and the longitudinal location lobes 22 (as described above with reference to FIGS. 11 and 12) which provide guides that make is easier for a kit user to 'correctly' longitudinally place the clip 3 with respect to the external tubular scaffold along a general line of direction C-C of a central axis of rotation of the external tubular scaffold 4.

Figures 15, 16:
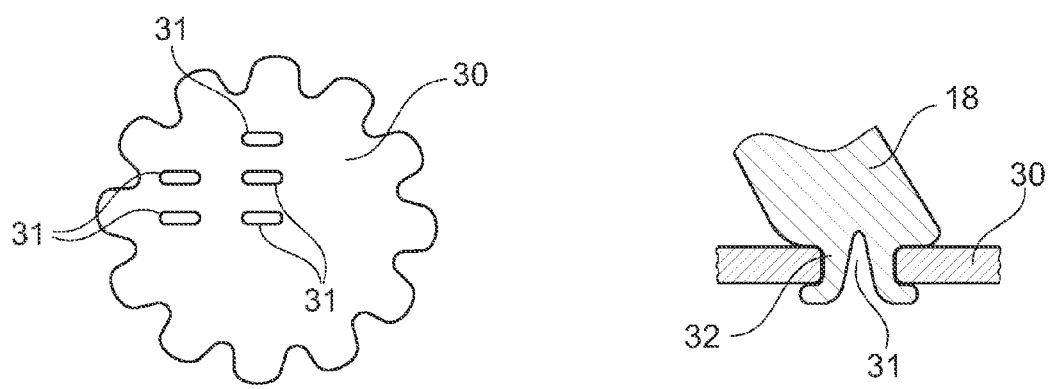
FIG. 15 Schematic representation of a steadying plate according to the invention.
FIG. 16 Schematic sectional representation of a snap-in/snap-out locator tab.

FIG. 15 and FIG. 16 show embodiments of a steadying plate 30 for use in an anastomosis kit of the invention. The steadying plate 30 may be made of any suitable material and has the purpose of adding weight and stability to the external tubular scaffold 4 and the removable scaffold handle 7,18,19 during application. Preferably, the steadying plate 30 may be made from a stainless steel material and may be between 2 mm and 20 mm thick. In use, a suitable locator such as a tab 32 on the removable scaffold handle 7,18,19 may be inserted in any of several provided suitable positional holes 31 in the steadying plate 30. The edge of the steadying plate 30 may be formed such that it can 'grip' into its surroundings when placed on an operation site, but such that it does not cause damage to the operation site. One suitable edge configuration is shown in FIG. 15, in which the edge is shaped in a curved, substantially circumferentially sinusoid manner. The shape of the steadying plate 30 helps it to lodge in the tissue in order to stabilise the external tubular scaffold 4. The steadying plate 30 may also be made of a sufficient size to allow the plate to be located under the user's (i.e. surgeon's) hand in use. The suitable locator, such as a tab 32, on the removable scaffold handle 7,18,19 may be made such that it locates in the steadying plate 30 in a snap-in/snap-out manner as depicted in FIG. 16.

In other embodiments (not shown) a clip may be provided on the removable scaffold handle 7,18,19 to allow the easy, removable attachment of various forms of handle extensions (e.g. rods, plates etc.) to the handle, which help a user in steadying the device in use. Such extensions may snap-on/snap-off to the removable scaffold handle.

Figure 17:
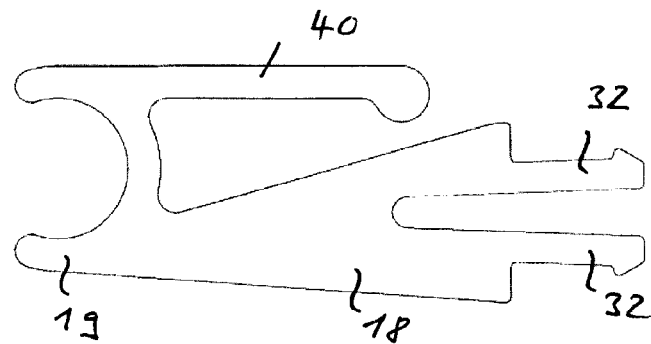
FIG. 17 Schematic representation of a further embodiment of a snap-on/snap-off removable scaffold handle.

FIG. 17 shows a further removably attachable removable scaffold handle 18,19, which can be used as disclosed in the embodiments shown in FIG. 10A to 10C. Similar to the scaffold handle 18,19 disclosed in FIG. 10D, the scaffold handle 18, 19 disclosed in FIG. 17 also comprises a generally 'C'-shaped portion 19 so that the removable scaffold handle 18 may be snapped onto and snapped off of the second longitudinal section 20. The scaffold handle 18, 19 disclosed in FIG. 17 further comprises a pivotable lever 40, to manually open the 'C'-shaped portion 19 by applying a force onto the lever 40, so that the scaffold handle 18 may be gently connected with and/or gently removed from the second longitudinal section 20 of the tubular scaffold 4. The scaffold handle 18 may also comprises a tab 32, as described in FIG. 10D.

FIGS. 18A, 18B, 18C show a further clip applicator 21, which comprises two rests 41 as well as two holding sections 42, on which, by using the fingers, a holding force F7 is applied. The effect of the rests 41 is disclosed in FIGS. 18A, 18B and 18C. Starting with the open position disclosed in FIG. 18A, a holding force F7 is applied onto the holding section 42, so that the clip applicator 21 and its tips 43 are moved in closing direction F8, so that the clip 3 gets closed, as shown in FIG. 18B. As shown in FIG. 18C, by increasing the holding force F7, the two rests 41 get in contact with each other, and the tips 43, by moving in opposite direction F9, open and release the clip 3. The clip applicator 21 may then be withdrawn.

Figure 19A:
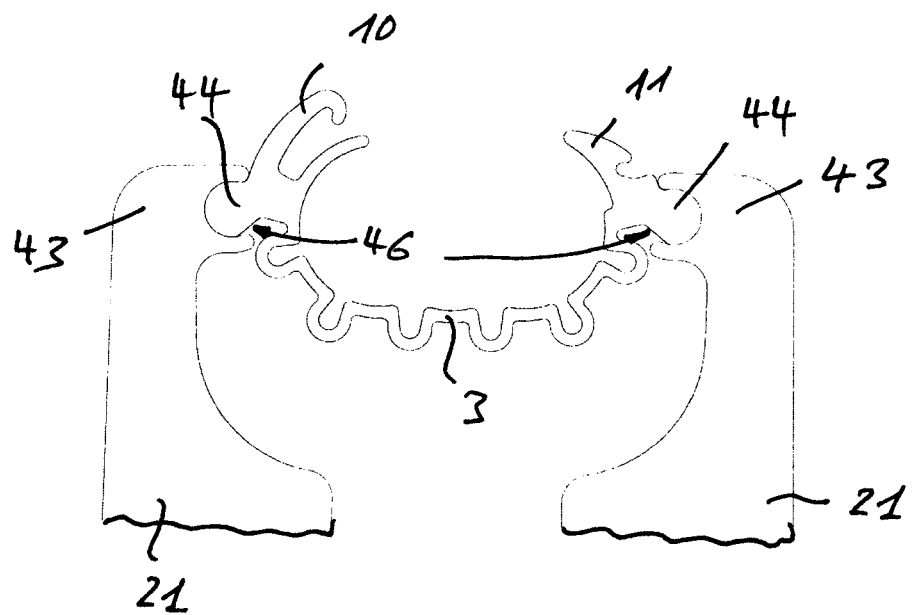
FIGS. 19A, 19B, 19C Detailed representations of the clip and clip applicator disclosed in FIGS. 18A, 18B and 18C.
Figure 19B:
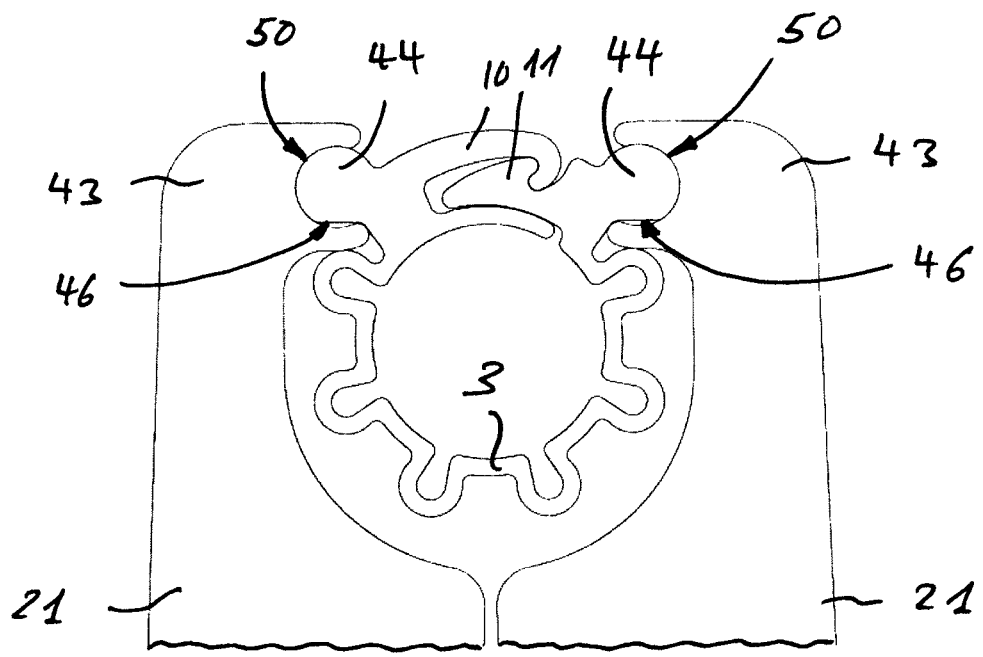
Figure 19C:
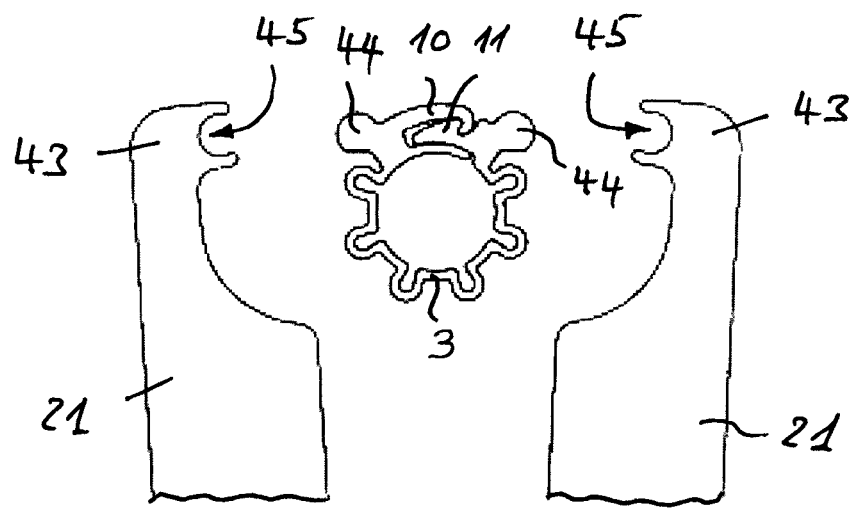

In the embodiment shown in FIGS. 19A, 19B and 19C, applicator locator lobes 44 are provided on the clip 3 and corresponding clip locator recesses 45 are provided on the clip applicator 21. The clip 3 also has a locking device 10,11 which consists of a male interlocking feature 10 and a female interlocking feature 11. In a preferred embodiment, the applicator locator lobes 44 may have generally cross-sectionally arcuate surfaces section 50 and the clip locator recesses 45 may have corresponding generally arcuate surfaces such that the applicator locator lobes 44 may preferably snap-in/snap-out of the clip locator recesses 45. In the embodiment shown in FIGS. 19A, 19B and 19C, as well as being snap-in/snap-out in the plane depicted in FIGS. 19A, 19B and 19C, the interrelationship between the applicator locator lobes 44 and the clip locator recesses 45 is such that the clip 3, may be moved (slid) into engagement with the clip applicator 21 in the direction substantially perpendicular to the plane depicted in FIGS. 19A, 19B and 19C.

In other desirable embodiments (not shown), the applicator locator lobes 44 and the clip locator recesses 45 may be formed such that the clip 3, may be moved (slid) into engagement with the clip applicator 21 in the direction perpendicular to the plane shown in FIGS. 19A, 19B and 19C, while simultaneously being formed such that the applicator locator lobes 44 and the clip locator recesses 45 are then locked together (i.e. not able to snap-in/snap-out) in the plane shown in FIGS. 19A, 19B and 19C, at least when the clip applicator is in its open position (analogous to FIG. 19A).

As shown in FIGS. 19A, 19B and 19C, in an especially advantageous embodiment, the surfaces of the applicator locator lobes 44 may be shaped such that when the clip applicator is open (FIG. 19A), the applicator locator lobes 44 are held by, in particular snapped-in to, the clip locator recesses 45, but also such that when the clip applicator is closed (FIG. 19B), the applicator locator lobes 44 may subsequently slide freely out of the clip locator recesses 45 as the clip applicator 21 is re-opened (FIG. 19C). In the embodiment shown, this functionality is provided by the flattened sections 46 of the generally cross-sectionally arcuate surfaces 50 of the applicator locator lobes 44, although such functionality may also be achieved through other arrangements (not shown), such as through providing other suitable shapes of lobes/recesses and/or providing locator lobes on the applicator with corresponding recesses on the clip.

In a further advantageous embodiment (not shown), the concept of interrelated applicator locator lobes 44 and clip locator recesses 45, as described above with respect to the embodiment shown in FIGS. 19A, 19B and 19C, may be advantageously combined with the concept of longitudinal location lobes 22 as described above with respect to FIGS. 11A, 11B, 12, 13, 14A and 14B to provide a clip 3/clip applicator 21 interrelationship that, in use, on the one hand, allows a simple and accurate longitudinal positioning of the clip 3 with respect to the tubular scaffold 4 upon installation of the clip 3, together with, on the other hand, a secure and easily releasable engagement of the clip 3 with the clip applicator 21.

In the embodiment shown in FIGS. 19A, 19B, 19C, closing or opening forces that might be generated by the clip 3 are in a preferred embodiment of minor or no importance, because the clip 3 is held by the tips 43 of the clip applicator 21, and the movement of the tips 43 determines the movement of the applicator locator lobes 44, respectively the movement of the clip 3.

Figure 20:
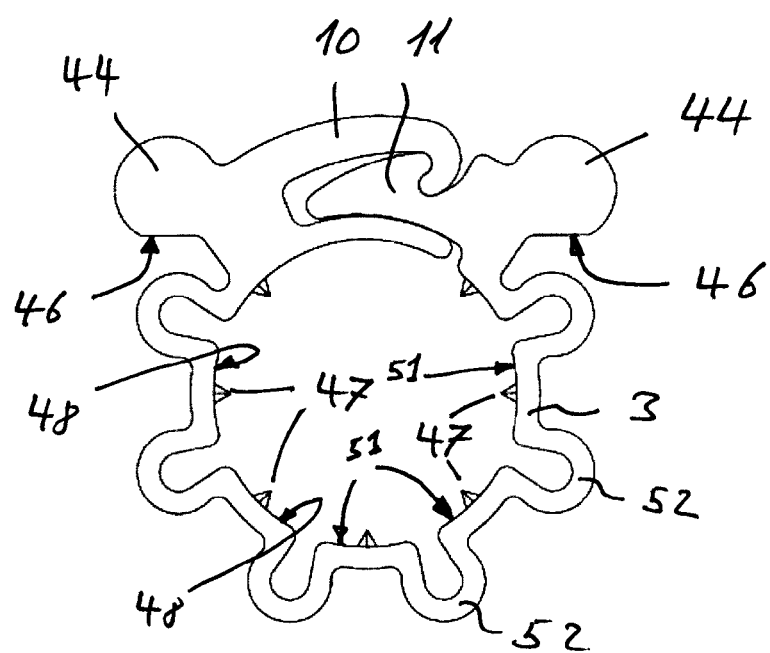
FIG. 20 Schematic representation of a further embodiment of a clip with locking devices.

FIG. 20 shows a further embodiment of a clip 3 with locking devices 10, 11, the clip 3 comprising a plurality of sections 48 with inwardly projecting spikes 47. The clip 3 is expandable in circumferential direction. The inwardly projection surface comprises a plurality of sectionally arcuate surfaces 51, which may comprise a spike 47. The clip 3 disclosed in FIG. 20 may also have no spikes 47 at all. The sectionally arcuate surface 51 might be of preferably non elastic material, and the arched sections 52 between the arcuate surfaces 51 might be flexible, so that the clip 3 is expandable in circumferential direction.

Figure 21:
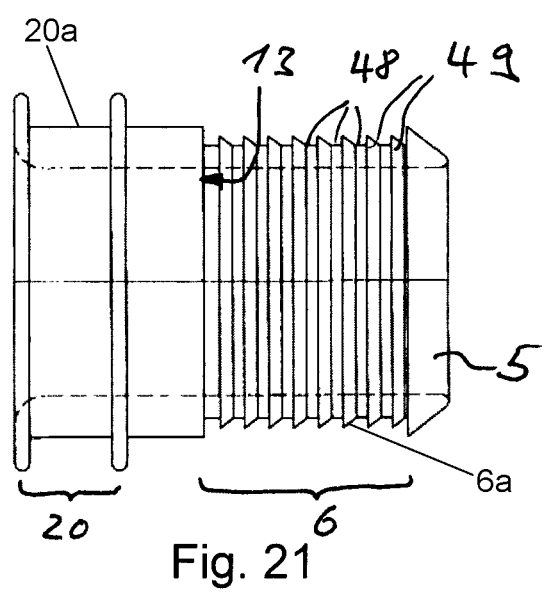
FIG. 21 Schematic representation of a further embodiment of a tubular scaffold.

FIG. 21 shows a further embodiment of a tubular scaffold 4, built very similar to the tubular scaffold 4 shown in FIG. 10C. The first longitudinal section 6 of the tubular scaffold 4 disclosed in FIG. 21 comprises a plurality of notches 48 and projecting rings 49. Otherwise the tubular scaffold 4 is build as disclosed in FIG. 10C. The projecting rings 49 improve the clamping of the tubular organs 1,2 between the outer surface of the first longitudinal section 6 and the inner surface of the clip 3.

A method for joining a first tubular organ (1), such as a blood vessel, to a second tubular organ (2), such as a blood vessel, using an anastomosis kit according to the present invention may comprise the steps of:

threading a longitudinal segment of the first tubular organ 1 through an interior passage of an external tubular scaffold 4, while using a removable scaffold handle 7,18,19 to hold the external tubular scaffold 4 and, optionally, using other steadying means such as a steadying plate 30 or handle extensions etc.;

folding the first tubular organ 1 back over itself to form a cuff portion 23 and placing the cuff portion 23 substantially concentrically around a first longitudinal tubular section 6 of the external tubular scaffold 4;

placing a longitudinal segment of the second tubular organ 2 substantially concentrically around at least a portion of the cuff portion 23;

mounting a clip 3 in a clip applicator 21;

using at least one of the clip applicator 21 and/or the external tubular scaffold 4 and/or the removable scaffold handle 7,18,19 and/or a longitudinal guide member to guide the clip 3 towards a particular longitudinal position 6 with respect to the external tubular scaffold 4 along a general longitudinal line of direction of a central axis of rotation of the external tubular scaffold 4;

using the clip applicator 21 to place and to close the clip 3 substantially concentrically around the second tubular organ 2 and the cuff portion 23 and the first longitudinal tubular section 6 such that the clip 3 embraces the second tubular organ 2 and the cuff portion 23 and the first longitudinal tubular section 6 and thereby holds together a longitudinal segment of an intima of the second tubular organ 2 and a longitudinal segment of an intima of the cuff portion 23;

using the clip applicator 21 to hold a completed joint comprising the joined tubular organs 1,2, the external tubular scaffold 4 and the clip 3 in a closed state;

using the clip applicator to provide an opposing force allowing removal of the removable scaffold handle 7, 18, 19;

using the clip applicator 21 to place the completed joint in a desired position prior to releasing the clip applicator 21.

The invention claimed is:

1. An intima-to-intima anastomosis kit comprising:
an external tubular scaffold (4) comprising a first longitudinal tubular section (6) having an outer surface (6a), and comprising a second longitudinal tubular section (20) having an outer surface (20a), the second longitudinal tubular section (20) being displaced longitudinally from the first longitudinal tubular section (6);
a clip (3) adapted to embrace the outer surface (6a) of the first longitudinal tubular section (6) when the clip (3) is in a closed state (24); and
a removable scaffold handle (18, 19), which, prior to a removal from the external tubular scaffold (4), is attached to the outer surface (20a) of the second longitudinal tubular section (20);
wherein at least immediately prior to said removal, said removable scaffold handle (18, 19) is snappably and removably attached to the outer surface (20a) of the second longitudinal tubular section (20) of the external tubular scaffold (4), and
wherein the clip (3) and the removable scaffold handle (18, 19) are adapted so that the removable scaffold handle (18, 19) being connected with the outer surface (20a) of the second longitudinal tubular section (20) while the clip (3) is attached and closed to embrace the outer surface (6a) of the first longitudinal tubular section (6), and
wherein a portion of the removable scaffold handle (18, 19) is generally 'C'-shaped (19) and is adapted to be snappably removable on and off of the outer surface (20a) of the second longitudinal tubular section (20) of the external tubular scaffold (4).

2. An intima-to-intima anastomosis kit according to claim 1, wherein, in the closed state (24), the clip (3) is generally 'O'-shaped, and in that the clip (3) is movable from an open state (25), in which the clip is generally 'C'-shaped to the closed state (24).

3. An intima-to-intima anastomosis kit according to claim 2, wherein the clip (3) comprises a locking device (10, 11), which holds the clip (3) in the closed state (24).

4. An intima-to-intima anastomosis kit according to claim 3, wherein the clip (3) is expandable in circumferential direction.

5. An intima-to-intima anastomosis kit according to claim 3 wherein the locking device (10, 11) is non-destructively-releasable and comprises at least one male interlocking feature (10) and at least one female interlocking feature (11), which interlocking features (10, 11) are adapted to interlock releasably with each other, whereby the clip (3) may be snapped shut into the closed state (24) and reopened without destruction of the clip (3).

6. An intima-to-intima anastomosis kit according to claim 1, wherein, in the closed state (24), the clip (3) is generally 'O'-shaped, and in that the clip (3) is movable from an open state (25), in which the clip is generally 'C'-shaped to the closed state (24) and in that, when the clip (3) is displaced from a clip rest state, at least one opposing clip returning force (F1, F2, F3) is generated that urges the clip (3) towards the clip rest state.

7. An intima-to-intima anastomosis kit according to claim 6 wherein the clip rest state substantially coincides with the open state (25), and in that the clip (3) is made of elastic material and is formed such that when the clip (3) is displaced from the clip rest state towards the closed state (24), an opposing clip-opening returning force (F3) is generated.

8. An intima-to-intima anastomosis kit according to claim 6 wherein the clip rest state substantially coincides with the closed state (24), and in that the clip (3) is made of elastic material and is formed such that when the clip (3) is displaced from the clip rest state towards an open state (25), a clip-closing returning force (F1) is generated.

9. An intima-to-intima anastomosis kit according to claim 1 wherein an interior clamping-surface (9) of the clip (3) and/or the outer surface (6a) of the first longitudinal section (6) is/are ribbed, fluted or otherwise unevenly textured such that when the clip (3) embraces the first longitudinal tubular section (6), a radial dimension of a substantially-circumferential clamping-gap (29) formed between the interior clamping-surface (9) and the exterior clamping-surface of the first longitudinal section (6) is thereby caused to vary in a circumferential direction and/or in a longitudinal direction.

10. An intima-to-intima anastomosis kit according to claim 1 wherein, when the clip (3) is in the closed state (24), the clip (3) may be displaced from a circumferential clip rest state in a circumferentially expansive direction, and in that the clip (3) is made of elastic material and is formed such that when the clip (3) is displaced from a circumferential clip rest state in a circumferentially expansive direction, an opposing, circumferentially-directed clip-constrictive returning force (F2) is generated.

11. An intima-to-intima anastomosis kit according to claim 1 wherein said intima-to-intima anastomosis kit further comprises a clip applicator (21) which releasably holds the clip (3).

12. An intima-to-intima anastomosis kit according to claim 11 wherein the clip (3) comprises applicator locator lobes (44) and that the clip applicator (21) comprises corresponding clip locator recesses (45), wherein the applicator locator lobes (44) and the clip locator recesses (45) are of such dimension and arranged such that the applicator locator lobes (44) may snap-in/snap-out of the clip locator recesses (45) and/or the applicator locator lobes (44) and the clip locator recesses (45) are of such dimension and arranged such that the applicator locator lobes (44) may move freely into or out of engagement with the clip locator recesses (45) in a first plane, but may subsequently not move freely with respect to each other in at least one second plane, said second plane(s) being substantially perpendicular to the first plane.

13. An intima-to-intima anastomosis kit according to claim 12 wherein the surfaces (50) of the applicator locator lobes (44) are shaped such that when the clip (3) is open, the applicator locator lobes (44) are held by the clip locator recesses (45), and when the clip (3) is closed, the applicator locator lobes (44) may subsequently slide freely out of the clip locator recesses (45) as the clip applicator (21) is re-opened.

14. An intima-to-intima anastomosis kit according to claim 11 further comprising means of at least one opposing clip returning force (F1, F2, F3) and/or by means of a clip applicator returning force (F5, F6), which is generated when the clip applicator (21) is displaced from a clip applicator rest state, and which urges the clip applicator (21) towards the clip applicator rest state.

15. An intima-to-intima anastomosis kit according to claim 14 wherein the clip (3) is releasably held in its open state (25) in the clip applicator (21).

16. An intima-to-intima anastomosis kit according to claim 14 wherein the clip (3) is releasably held at a predetermined longitudinal location with respect to the clip applicator (21) along a general longitudinal line of direction of a central axis of rotation (B-B) of the clip (3), and in that at least one of the clip applicator (21) and/or the external tubular scaffold (4) and/or the removable scaffold handle (18, 19) and/or a longitudinal guide member facilitates a guiding of the clip (3) towards a predetermined longitudinal position with respect the external tubular scaffold (4) along a general longitudinal line of direction (C-C) of a central axis of rotation of the external tubular scaffold (4).

17. An intima-to-intima anastomosis kit according to claim 1 wherein said intima-to-intima anastomosis kit further comprises a steadying plate (30) and in that the removable scaffold handle (18, 19) comprises locating means (32), whereby the removable scaffold handle (18, 19) may be removably attached to the steadying plate (30) at least one predetermined location with respect to the steadying plate (30).

* * * * *